(12) United States Patent
Gangwar et al.

(10) Patent No.: US 10,377,710 B2
(45) Date of Patent: Aug. 13, 2019

(54) PROCESS FOR THE PREPARATION OF CONSIDERABLY PURE SILODOSIN

(71) Applicant: Mankind Pharma LTD, New Delhi (IN)

(72) Inventors: Kuldeep Singh Gangwar, Haryana (IN); Anil Kumar, Haryana (IN); Bhuwan Bhashkar, Haryana (IN)

(73) Assignee: MANKIND PHARMA LTD., New Delhi (IN)

( * ) Notice: Subject to any disclaimer, the term of this patent is extended or adjusted under 35 U.S.C. 154(b) by 24 days.

(21) Appl. No.: 15/512,044

(22) PCT Filed: Sep. 10, 2015

(86) PCT No.: PCT/IB2015/056934
§ 371 (c)(1),
(2) Date: Mar. 16, 2017

(87) PCT Pub. No.: WO2016/042441
PCT Pub. Date: Mar. 24, 2016

(65) Prior Publication Data
US 2017/0362174 A1  Dec. 21, 2017

(51) Int. Cl.
*C07D 209/08* (2006.01)
*H01R 13/66* (2006.01)
*H01R 43/20* (2006.01)
*H01R 13/52* (2006.01)
*H01R 12/77* (2011.01)
*H01R 24/62* (2011.01)

(52) U.S. Cl.
CPC ......... *C07D 209/08* (2013.01); *H01R 12/777* (2013.01); *H01R 13/5202* (2013.01); *H01R 13/665* (2013.01); *H01R 24/62* (2013.01); *H01R 43/205* (2013.01); *H01R 13/521* (2013.01); *H01R 13/6658* (2013.01)

(58) Field of Classification Search
CPC .................................................... C07D 209/08
See application file for complete search history.

(56) References Cited

U.S. PATENT DOCUMENTS

| | | | |
|---|---|---|---|
| 7,834,193 B2 | 11/2010 | Yamaguchi et al. | |
| 2007/0197627 A1* | 8/2007 | Yamaguchi | C07D 209/08 514/415 |

FOREIGN PATENT DOCUMENTS

| CN | 101412690 A | * | 4/2009 | |
|---|---|---|---|---|
| WO | 2012131710 | | 10/2012 | |
| WO | WO-2012131710 A2 | * | 10/2012 | ........... C07D 209/08 |
| WO | 2012147019 | | 11/2012 | |
| WO | 2012147107 | | 11/2012 | |
| WO | WO-2012147019 A1 | * | 11/2012 | ........... C07D 209/24 |
| WO | WO-2012147107 A2 | * | 11/2012 | ........... A61K 31/404 |
| WO | WO-2016042441 A1 | * | 3/2016 | ........... C07D 209/08 |

OTHER PUBLICATIONS

Merriam-Webster, definition of isolate, obtained from https://www.merriam-webster.com/dictionary/isolate on Jun. 6, 2018 (Year: 2018).*
Encyclopedia Britannica, Separation and purification, https://www.britannica.com/science/separation-and-purification, accessed May 9, 2018 (Year: 2018).*
PCT International Search Report and Written Opinion, dated Oct. 28, 2015; PCT/IB2015/056934.

* cited by examiner

*Primary Examiner* — Matthew P Coughlin
(74) *Attorney, Agent, or Firm* — Maschoff Brennan (57) ABSTRACT

The present invention relates to a novel, improved, commercially viable and industrially advantageous process for the preparation of Silodosin of Formula (I), its pharmaceutically acceptable salts or solvates thereof. The invention relates to the preparation of considerably pure Silodosin with high yield.

11 Claims, 3 Drawing Sheets

Figure 1: IR spectrum

PROCESS FOR THE PREPARATION OF CONSIDERABLY PURE SILODOSIN

FIELD OF THE INVENTION

The present invention relates to a novel, improved, commercially viable and industrially advantageous process for the preparation of Silodosin of Formula (I), its pharmaceutically acceptable salts or solvates thereof. The invention relates to the preparation of considerably pure Silodosin with high yield.

Formula (I)

More particularly, the present invention provides an industrially applicable novel process for preparation of considerably pure Silodosin which includes conversion of chiral compound, 3-{7-cyano-5-[(2R)-2-aminopropyl]-2,3-dihydro-1H-indol-1-yl}propyl benzoate to Silodosin wherein, the N,N-dialkyl impurity of Formula (IIc) is removed at last stage of the production process i.e. at crude Silodosin.

Formula (II)

IIa: R = CN, R' = Bz
IIb: R = CN, R' = H
IIc: R = CONH₂, R' = H

BACKGROUND OF THE INVENTION

Silodosin, 1-(3-hydroxypropyl)-5-[(2R)-2-({2-[2-(2,2,2-trifluoroethoxy)phenoxy]ethyl}amino)propyl]-2,3-dihydro-1H-indole-7-carboxamide of Formula (I) is an indoline antidysuric which has a selectively inhibitory effect against urethra smooth muscle constriction, and decreases urethra internal pressure without great influence on blood pressure. Silodosin is available under trade names RAPAFLO® or UROREC®. Silodosin was first disclosed in EP 0600675 as a therapeutic agent for the treatment of dysuria associated with benign prostatic hyperplasia, where a process for producing the compound is also disclosed.

Formula (I)

Since, Silodosin is an optically active compound having a complex chemical structure; its synthesis is relatively complex and requires a sequence of multiple steps.

U.S. Pat. No. 6,310,086, discloses a process for preparing Silodosin analogue compound from reaction of (R)-3-{5-(2-aminopropyl)-7-cyano-2,3-dihydro-1H-indol-1-yl}propylbenzoate with 2-(2-ethoxyphenoxy)ethyl methanesulfonate and finally isolated as a crude compound which is purified by column chromatography. The said process has a major disadvantage of using column chromatography which is not feasible at plant scale production.

PCT application no. WO 2012147019, discloses the preparation of Silodosin as shown in scheme-1, wherein the N,N-dialkyl impurity of Formula (IIa) formed during condensation of 3-{7-cyano-5-[(2R)-2-aminopropyl]-2,3-dihydro-1H-indol-1-yl}propyl benzoate of Formula (III) with 2-(2-(2,2,2-trifluoroethoxy)phenoxy)ethyl methanesulfonate of Formula (IV); is removed through preparation of monotartarate salt to give compound of Formula (VI). The compound of Formula (VI) is base hydrolyzed followed by cyano hydrolysis to give crude Silodosin of Formula (VIII) which is then further purified by crystallization to get desired pure Silodosin.

Scheme-1:

(VII)

(VI)

crystallisation → Pure Silodosin Formula (I)

(VIII)
crude Silodosin

Va: n = 1
IIa: n = 2

Major drawback of above said reaction process is that multiple isolations and crystallizations are required to get pure Silodosin.

Similarly, U.S. Pat. No. 7,834,193 discloses monooxalate salt represented by Formula VIa having 0.9% of dialkyl impurity represented by Formula IIa. The oxalate salt so obtained is subjected to alkaline hydrolysis followed by transformation of the nitrile to an amide.

Formula (VIa)

Similarly, PCT application no. WO 2012147107, discloses the method wherein Silodosin is prepared by condensation of 3-{7-cyano-5-[(2R)-2-aminopropyl]-2,3-dihydro-1H-indol-1-yl}propyl benzoate with 2-[2-(2,2,2-trifluoroethoxy)phenoxy]ethyl methanesulfonate in solvent using base and phase transfer catalyst wherein, dialkyl impurity is formed up to 11%, followed by hydroxyl deprotection in protic solvent using base and phase transfer catalyst which is then subjected to purification to remove N,N-dialkyl impurity represented by Formula (IIb) up to 0.6% through the preparation of acetate salt. This process suffers from a serious drawback i.e., accountable formation of dialkyl impurity and even after purification the impurity is reduced to only up to 0.6%. Secondly, the process requires multiple isolations and purifications ensuing into time engulfing work-ups and purifications and hence incurring solvent wastage. This makes process lengthy, uneconomical and tedious to be performed at plant scale.

Another PCT application no. WO 2012131710, discloses the preparation of Silodosin in which the chiral compound (3-(5-((R)-2-aminopropyl)-7-cyanoindolin-1-yl)propyl benzoate) is reacted with 2-[2-(2,2,2-trifluoroethoxy)phenoxy] ethyl methane sulfonate in isopropyl alcohol using sodium carbonate as base. The reaction is completed in 40-50 h and about 9-11% of dimer is formed during condensation. After completion of reaction, it is subjected to hydroxyl deprotection and the crude compound so obtained is purified to remove the N,N-dialkyl impurity of Formula (IIb). The pure compound is then reacted with hydrogen peroxide in dimethyl sulfoxide to give Silodosin. The major drawback of this process is that the process is a multistep process wherein the condensation reaction is long-drawn-out resulting into countable amount of dimer formation during the process.

Thus, the prior art methods of preparing Silodosin require multiple and repeated purifications to synthesize DMF (Drug Master File) grade Silodosin. None of the prior art produces compound of Formula (VI) or (VII) with N,N-dialkyl impurity of Formula (IIa) or (IIb) in an amount less than 0.6% to 0.5% even after purification. Therefore to prepare highly pure Silodosin, there is a need to explore new synthetic schemes that could be more economical and scalable. The present invention provides a novel, improved, commercially viable and industrially advantageous process for the synthesis of Silodosin and its pharmaceutically acceptable salts or solvates thereof. The present invention focus on preparation of highly pure Silodosin in appreciable yields with minimal use of solvents wherein the Silodosin is isolated with purity ≥99.5% having N,N-dialkyl impurity less than 0.03% and other individual impurities below 0.1%.

OBJECT AND SUMMARY OF THE INVENTION

It is the principle object of the present invention to improve upon the shortcomings in the prior art by providing an improved process for preparing Silodosin of Formula (I), which is employed for the treatment of dysuria associated with benign prostatic hyperplasia.

Formula (I)

Another object of the present invention is to provide a novel process for the preparation of considerably pure Silodosin wherein the process employs minimal use of solvents, purification steps and wastage of material.

It is yet another object of the present invention to provide a process for the preparation of Silodosin which is cost effective, environmental friendly, easy to implement in industry with good yield and high purity.

To solve the above mentioned objects, the present applicant explored the chemistry and achieved a considerably pure Silodosin with purity ≥99.5% by eliminating the N,N-dialkyl impurity at last stage of production process (i.e., at crude Silodosin) wherein the dialkyl impurity is removed up to less than 0.03%, thereby forming the basis of the present invention.

Accordingly, the present invention provides an improved process for the preparation of Silodosin represented by Formula (I), its pharmaceutical acceptable salts or solvates.

In first aspect, the present invention provides a process for the preparation of Silodosin represented by Formula (I)

Formula (I)

which comprises the steps of:
a) condensing chiral compound represented by Formula (III)

Formula (III)

wherein, Bz represents to Benzoyl group, with compound represented by Formula (IV)

Formula (IV)

wherein, Ms represents to Methanesulfonyl group, in presence of base and phase transfer catalyst in an organic solvent to give intermediate represented by Formula (V)

Formula (V)

wherein, n is an integer of 1 and 2 and Bz is as defined above:
b) optionally isolating compound of Formula (V),
c) without purification converting the compound of Formula (V) to de-protected compound represented by Formula (IX) in an organic solvent;

Formula (IX)

wherein, n is as defined above;
d) optionally isolating compound of Formula (IX),
e) without purification converting the compound of Formula (IX) to compound represented by Formula (X)

Formula (X)

wherein n is as defined above;
f) subjecting the compound of Formula (X) to purification by converting to acid salt for removal of N,N-dialkyl impurity represented by Formula (IIc); and Formula (IIc)

g) hydrolysis of the said acid salt to get Silodosin of Formula (I) with purity ≥99.5%.

In the second aspect, the present invention relates to the preparation of Silodosin of Formula (I) which comprises of:
a) one pot conversion of compound of Formula (III) to hydroxyl compound of Formula (IX) without isolation of intermediates which is then in situ converted to crude Silodosin of Formula (X) followed by purification through acid salt preparation gives compound of Formula (I) with N,N-dialkyl impurity of Formula (IIc) in an amount of less than 0.03% and other individual impurities below 0.1%; or
b) conversion of compound of Formula (III) to condensed product of Formula (V) which without any purification is converted to crude Silodosin of Formula (X) in a single pot followed by purification performed in accordance to the present invention.

In a further aspect, the present invention provides a process for the preparation of Silodosin represented by Formula (I), by purification of crude Silodosin of Formula (X) through oxalic acid salt preparation resulting into compound of Formula (I) with N,N-dialkyl impurity of Formula (IIc) in an amount of less than 0.03% and other individual impurities below 0.1%.

The above and other objects of the present invention are further attained and supported by the following embodiments described herein. However, the desired embodiments are in accordance with the best mode of practice and the scope of the invention is not restricted to the described embodiments herein after.

DETAILED DESCRIPTION OF THE INVENTION

Figure 1:
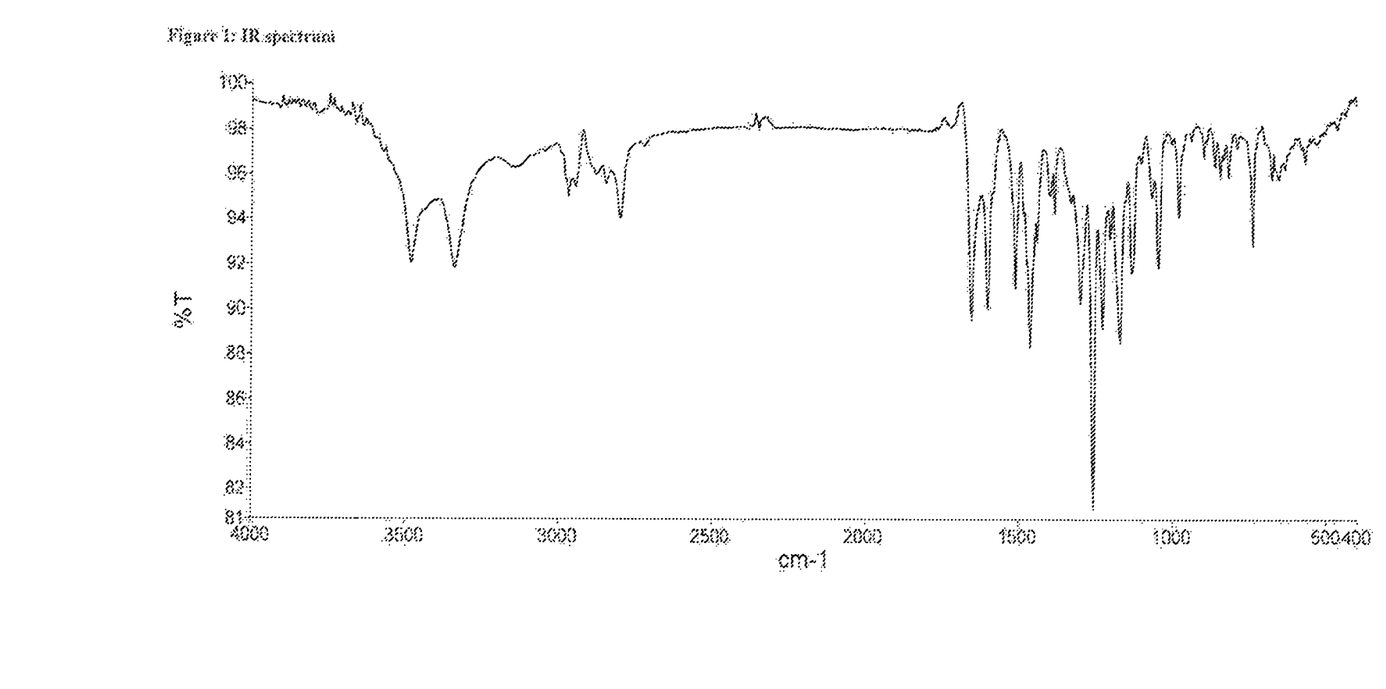
FIG. 1 is a graph showing an IR pattern of crystal form of above disclosed Silodosin of Formula (I) characterized by main bands at about 3481, 3338, 3968, 2799, 1651, 1597, 1459, 1507, 1378, 1253, 1223, 1166, 1044, 735 cm$^{-1}$.
Figure 2:
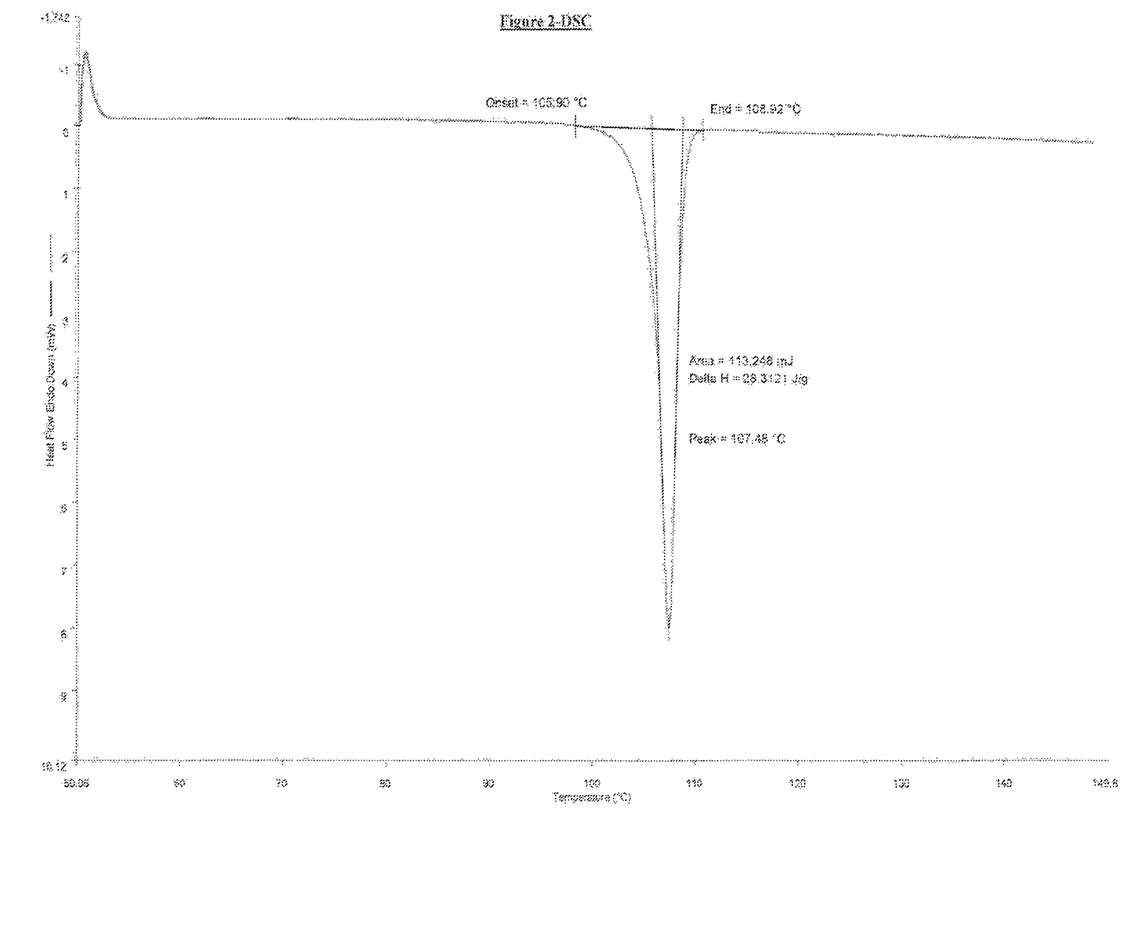
FIG. 2 is a graph showing DSC pattern of crystal form of above disclosed Silodosin of Formula (I).
Figure 3:
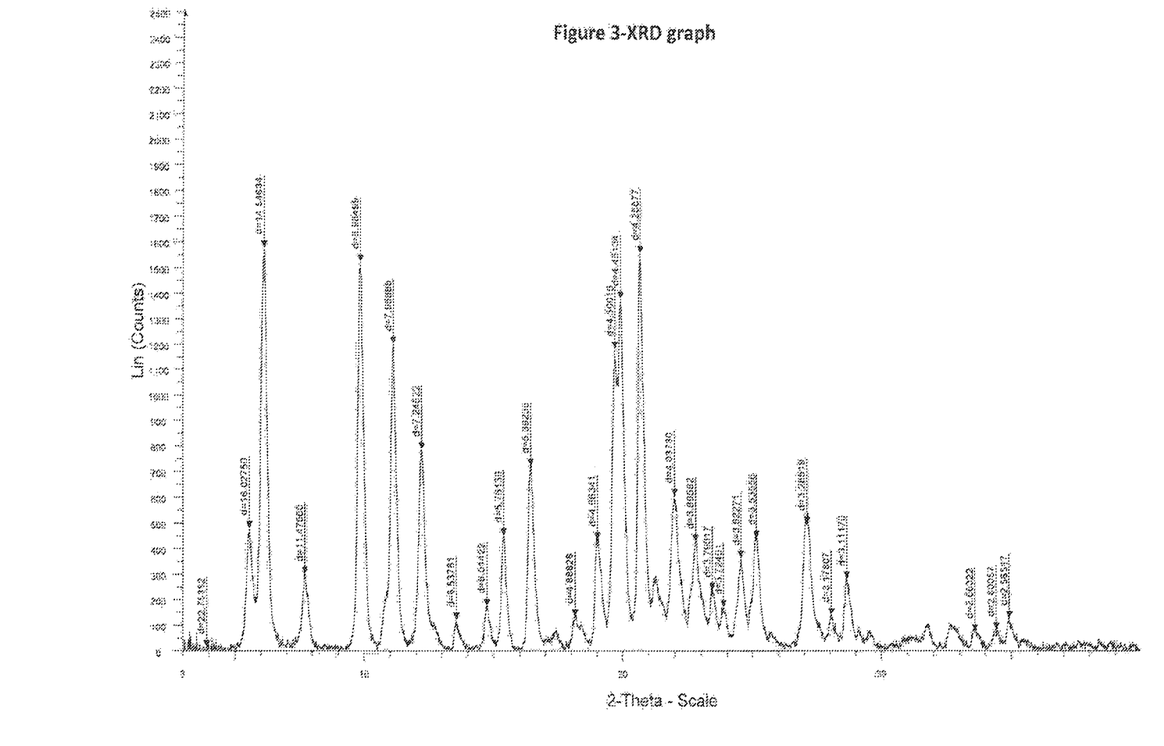
FIG. 3 is a graph showing X-ray powder diffraction of crystal form of above disclosed Silodosin of Formula (I) having 2 theta angle position at about 5.51, 6.07, 9.83, 11.11, 12.20, 14.72, 15.36, 16.42, 19.01, 19.71, 20.69, 21.99, 22.80, 25.18, 27.14 and 28.69±0.2 degrees two-theta.

While the invention is susceptible to various modifications and alternatives, specific embodiment thereof will be described in detail below. The steps of a method may be providing more details that are pertinent to understanding the embodiments of the present invention and so as not to obscure the disclosure with details that will be readily apparent to those of ordinary skills in the art having benefit of the description herein.

Further characteristics and advantages of the process according to the invention will result from the description herein below of preferred exemplary embodiments, which are given as indicative and non-limiting examples.

The term "Crude Silodosin" referred herein relates to Silodosin obtained by any of methods given in Example 1 of the present invention, viz. Method A to Method G or obtained by prior art methods, in which Silodosin has a purity less than 99.5% with impurity like N,N-dialkyl impurity in an amount ≥1% as measured by HPLC.

The term "Considerably pure" referred in the present specification relates to Silodosin of Formula (I) or a process for preparation thereof, in which Silodosin has a purity ≥99.5% with impurities like N,N-dialkyl compound of Formula (IIc) is in an amount of less than about 0.03% and other impurities below 0.1% as measured by HPLC.

The term "HPLC" referred in the present specification relates to High-performance liquid chromatography having following specification:

HPLC Condition:

Mobile phase-A: Dissolve 1.36 g of potassium dihydrogen orthophosphate in 1000 ml of water; add 2.0 ml of triethyl amine. Adjust the pH 2.5 with orthophophoric acid.

Mobile phase-B: Acetonitrile:water (80:20)

Diluent: Water:Acetonitrile (1:1)

Column: Inertsil ODS-3, 250×4.6 mm, 3μ

Column oven temp.: 45° C.

Flow rate: 1.0 ml/min

Detection: 270 nm

Run time: 50.0 min

RRT of impurity: 1.90

The present invention provides an improved and industrially advantageous process for the preparation of Silodosin of Formula (I), its pharmaceutically acceptable salts or solvates thereof.

According to the present invention there is provided an improved method of production of DMF (Drug Master File) grade of Silodosin, with use of minimal amount of solvents, high purity and yield, economical, which is applicable at large scale production.

In accordance to one embodiment of the present invention, the process of the preparation of Silodosin represented by Formula (I)

Formula (I)

comprises the steps of:
a) condensing chiral compound represented by Formula (III)

Formula (III)

wherein, Bz represents to Benzoyl group with compound represented by Formula (IV)

Formula (IV)

wherein, Ms represents to Methanesulfonyl group in presence of base and phase transfer catalyst in an organic solvent to give intermediate represented by Formula (V)

Formula (V)

wherein, n is an integer of 1 and 2 and Bz is as defined above, wherein the compound having n=2 is formed in an amount of less than 5%;

b) optionally isolating compound of Formula (V), c) without purification converting it to de-protected compound represented by Formula (IX) in an organic solvent;

Formula (IX)

wherein, n is as defined above;

d) optionally isolating compound of Formula (IX), and e) without purification converting it to compound represented by Formula (X)

Formula (X)

wherein n is as defined above;

f) subjecting compound of Formula (X) to purification by converting to acid salt for removal of N,N-dialkyl impurity represented by Formula (IIc);

Formula (IIc)

g) hydrolysis of the said acid salt to get Silodosin of Formula (I) with purity ≥99.5%.

In accordance to other embodiment of the present invention, the organic solvent used in step (a) and (c) is selected from the group comprising of benzene, toluene, o-xylene, m-xylene, p-xylene, acetonitrile, dimethyl sulfoxide, methyl isobutyl ketones, dioxane, dimethyl formamide, dimethyl acetamide, N-methyl pyrrolidone and/or mixture thereof. More preferably, the solvent selected is toluene and/or dimethyl sulfoxide.

The suitable base for step (a) is selected from the group comprising of hydroxides, carbonates, alkoxides, phosphates, such as sodium hydroxide, potassium hydroxide, sodium carbonate, sodium bicarbonate, potassium carbonate, potassium bicarbonate, potassium dihydrogen phosphate, dipotassium hydrogen phosphate, potassium tert-butoxide, sodium tert-butoxide, sodium methoxide, cesium carbonate, or mixture thereof. More preferably, the base is dipotassium hydrogen phosphate.

The said phase transfer catalyst is selected from crown ether, triglyme, tetrabutyl ammonium bromide, tetrabutyl ammonium chloride, tetrabutyl ammonium iodide, potassium fluoride and the like. Preferably the phase transfer catalyst is tetrabutyl ammonium iodide.

The condensation in step (a) is carried out at temperature range of 25° C. to 100° C. Preferably the condensation is carried out at 80° C.–110° C. More preferably, the condensation is carried out at 85° C. to 90° C.

In accordance to other embodiment of the present invention, the N,N-dialkyl impurity of Formula IIa is formed in an amount less than 5%, preferably in the range of 1 to 5%.

In accordance to another embodiment of the present invention, the de-protection in step (b) is performed with or without isolation of the condensed intermediate of Formula (V) in a base like hydroxides, preferably sodium hydroxide wherein, the said compound of Formula (V) is a mixture of monoalkylated compound of Formula Va (n=1) and dialkylated compound of Formula IIa (n=2).

In accordance to one another embodiment of the present invention, the de-protected compound of formula (IX) may or may not be isolated and is subjected to nitrile conversion to amide to give crude Silodosin of Formula (X) wherein, the transformation is carried out using hydrogen peroxide in a solvent like dimethyl sulfoxide.

It may be noted that the N,N-dialkyl impurity represented by Formula (Ia) formed during condensation in step (a) is not isolated at any intermediate stage. Hence in step (b), the hydroxyl group of monoalkylated and dialkylated product is deprotected together to give compound of Formula (IX) wherein, Formula (IX) represents mixture of monoalkylated product of Formula (IXa; n=1) and dialkylated impurity of Formula (IIb) with dialkyl impurity in the range of 1 to 5%. Similarly, no purification is performed at step (b) and hence in step (c) nitrile of the compound represented by Formula (IX) is converted to amide to give corresponding product of Formula (X), wherein Formula (X) represents mixture of monoalkylated product of Formula (Xa; n=1) and dialkylated impurity of Formula (IIc) having dialkyl impurity in the range of 1 to 5%.

In accordance to a preferred embodiment of the present invention, the said acid salt prepared in step (f) is an oxalic acid salt wherein, the salt preparation is meant for the removal of N,N-dialkyl impurity of Formula (IIc).

In accordance to yet further embodiment of the present invention, the N,N-dialkyl impurity is reduced to an amount less than 0.03%, preferably in an amount ranging 0.01% to 0.03%.

In accordance to furthermore embodiment of the present invention, the Silodosin obtained after salt hydrolysis in step (e), is considerably pure with purity ≥99.5% wherein all the individual impurities are below 0.1% as measured by HPLC.

The process of the present invention is short, easy to handle, reproducible and scalable. Thus the process is industrially applicable and economical in nature.

The starting materials, viz. compounds of Formula (III) and Formula (IV) may be prepared by conventional methods.

EXAMPLES

The invention is explained in detail in the following examples which are given solely for the purpose of illustration only and therefore should not be construed to limit the scope of the invention.

Example 1

Preparation of Crude Silodosin

Method A:

To the solution of 10 g (0.0275 mol) of (3-(5-((R)-2-aminopropyl)-7-cyanoindolin-1-yl)propyl benzoate) in 100 ml of toluene was added 14.3 g (0.0826 mol) of dipotassium hydrogen phosphate and 8.20 g (0.0261 mol) of 2-[2-(2,2,2-trifluoroethoxy)phenoxy]ethyl methane sulfonate followed by addition of 2.0 g (0.0055 mol) of tetrabutyl ammonium iodide and stirred the reaction mass at 85-90° C. for 10-12 h. Cooled the reaction mass, added de-mineralized water and separated the toluene layer followed by distillation to get crude viscous mass. Added 110 ml of dimethyl sulfoxide and a solution of 1.51 g (0.0415 mol) of sodium hydroxide dissolved in 8.52 ml of water followed by addition of 6.42 g (0.0567 mol) of 30% w/w of hydrogen peroxide. Stirred the reaction mass at 20-25° C. till completion and added sodium sulfite solution. Extracted the compound in ethylacetate, washed the organic layer with brine solution and concentrated to get 10.2 g of crude Silodosin.
N,N-dialkyl impurity is 3.2% as per HPLC.
Method B:

To the solution of 10 g (0.0275 mol) of (3-(5-((R)-2-aminopropyl)-7-cyanoindolin-1-yl)propyl benzoate) in 100 ml of toluene was added 14.3 g (0.0826 mol) of dipotassium hydrogen phosphate and 8.20 g (0.0261 mol) of 2-[2-(2,2,2-trifluoroethoxy)phenoxy]ethyl methane sulfonate followed by addition of 2.0 g (0.0055 mol) of tetrabutyl ammonium iodide and stirred the reaction mass at 85-90° C. for 10-12 h. Added solution of 4.4 g of sodium hydroxide dissolved in 10 ml of water and stirred the reaction at ambient temperature till completion. Quenched the reaction mass with water and separated the layers. Washed the toluene layer with brine and concentrated under reduced pressure to get crude mass. Dissolved the crude mass so obtained in 110 ml of dimethyl sulfoxide and added a solution of 1.95 g (0.0488 mol) of sodium hydroxide dissolved in 7.95 ml of water followed by addition of 7.5 g (0.066 mol) of 30% w/w of hydrogen peroxide. Stirred the reaction mass at room temperature followed by addition of 210 ml of aqueous solution of sodium sulfite and extracted the compound in ethyl acetate. Washed the organic layer with brine and concentrated under reduced pressure to get 10.1 g of crude Silodosin.
N,N-dialkyl impurity is 3.0% as per HPLC
Method C:

To the solution of 10 g (0.0275 mol) of (3-(5-((R)-2-aminopropyl)-7-cyanoindolin-1-yl)propyl benzoate) in 100 ml of dimethyl sulfoxide was added 14.3 g (0.0826 mol) of dipotassium hydrogen phosphate and 8.20 g (0.0261 mol) of 2-[2-(2,2,2-trifluoroethoxy)phenoxy]ethyl methane sulfonate followed by addition of 2.0 g (0.0055 mol) of tetrabutyl ammonium iodide and stirred the reaction mass at 85-90° C. for 2-3 h. Added 100 ml of water and 50 ml of toluene and stirred the reaction mass at room temperature for half an hour. Separated the toluene layer and concentrated under reduced pressure. To the crude mass so obtained was added 110 ml of dimethyl sulfoxide and a solution of 4.4 g of sodium hydroxide dissolved in 10 ml of water followed by addition of 7.5 g (0.066 mol) of 30% w/w of hydrogen peroxide. Stirred the reaction mass at room temperature followed by addition of 210 ml of aqueous solution of sodium sulfite and extracted the compound in ethyl acetate. Washed the organic layer with brine and concentrated under reduced pressure to get 9.8 g of crude Silodosin.
N,N-dialkyl impurity is 2.1% as per HPLC
Method D:

To the solution of 20 g (0.055 mol) of (3-(5-((R)-2-aminopropyl)-7-cyanoindolin-1-yl)propyl benzoate) in 200 ml of toluene was added 28.6 g (0.165 mol) of dipotassium hydrogen phosphate and 16.4 g (0.0522 mol) of 2-[2-(2,2,2-trifluoroethoxy)phenoxy]ethyl methane sulfonate followed by addition of 4.0 g (0.11 mol) of tetrabutyl ammonium iodide and stirred the reaction mass at 85-90° C. for 10-12 h. Added de-mineralized water and stirred at room temperature for half an hour. Separated the toluene layer to which was added a solution of 8.8 g of sodium hydroxide dissolved in 20 ml of water and stirred the reaction at ambient temperature till completion. Quenched the reaction mass with water and separated the layers. Washed the toluene layer with brine and concentrated under reduced pressure to get crude mass. Dissolved the crude mass so obtained in 200 ml of dimethyl sulfoxide and added a solution of 3.9 g (0.0976 mol) of sodium hydroxide dissolved in 16 ml of water followed by addition of 15 g (0.132 mol) of 30% w/w of hydrogen peroxide. Stirred the reaction mass at room temperature followed by addition of 400 ml of aqueous solution of sodium sulfite and extracted the compound in ethyl acetate. Washed the organic layer with brine and concentrated under reduced pressure to get 21.0 g of crude Silodosin.
N,N-dialkyl impurity is 2.8% as per HPLC
Method E:

To the solution of 2 g (0.0055 mol) of (3-(5-((R)-2-aminopropyl)-7-cyanoindolin-1-yl)propyl benzoate) in 20 ml of was dimethyl sulfoxide was added 2.87 g (0.0165 mol) of dipotassium hydrogen phosphate and 1.64 g (0.0052 mol) of 2-[2-(2,2,2-trifluoroethoxy)phenoxy]ethyl methane sulfonate followed by addition of 0.29 g (0.0011 mol) of 16-crown ether and stirred the reaction mass at 85-90° C. for 10-12 h. Added a solution of 0.88 g of sodium hydroxide dissolved in 2 ml of water and stirred the reaction at ambient temperature till completion. Added de-mineralized water and toluene and stirred at room temperature for half an hour. Separated the toluene layer and concentrated under reduced pressure and to the solid mass so obtained were added 20 ml of dimethyl sulfoxide and a solution of 0.38 g (0.0231 mol) of sodium hydroxide dissolved in 1.6 ml of water followed by addition of 1.5 g (0.0132 mol) of 30% w/w of hydrogen peroxide. Stirred the reaction mass at room temperature followed by addition of aqueous solution of sodium sulfite and extracted the compound in ethyl acetate. Washed the organic layer with brine and concentrated under reduced pressure to get 2.1 g of crude Silodosin.
N,N-dialkyl impurity is 2.2% as per HPLC Method F:

To the solution of 10 g (0.0275 mol) of (3-(5-((R)-2-aminopropyl)-7-cyanoindolin-1-yl)propyl benzoate) in 100 ml of was acetonitrile was added 14.3 g (0.0826 mol) of dipotassium hydrogen phosphate and 8.20 g (0.0261 mol) of 2-[2-(2,2,2-trifluoroethoxy)phenoxy]ethyl methane sulfonate followed by addition of 2.0 g (0.0055 mol) of tetra butyl ammonium iodide and stirred the reaction mass at 85-90° C. for 10-12 h. Added a solution of 4.4 g of sodium hydroxide dissolved in 10 ml of water and stirred the reaction at ambient temperature till completion. Added demineralized water and toluene and stirred at room temperature for half an hour. Separated the toluene layer and concentrated under reduced pressure and to the solid mass so obtained were added 110 ml of dimethyl sulfoxide and a solution of 1.95 g (0.0488 mol) of sodium hydroxide dissolved in 7.95 ml of water followed by addition of 7.5 g (0.066 mol) of 30% w/w of hydrogen peroxide. Stirred the reaction mass at room temperature followed by addition of 210 ml of aqueous solution of sodium sulfite and extracted the compound in ethyl acetate. Washed the organic layer with brine and concentrated under reduced pressure to get 9.5 g of crude Silodosin.
N,N-dialkyl impurity is 3.1% as per HPLC Method G:

To the solution of 10 g (0.0275 mol) of (3-(5-((R)-2-aminopropyl)-7-cyanoindolin-1-yl)propyl benzoate) in 100 ml of was Dimethyl sulfoxide was added 14.3 g (0.0826 mol) of dipotassium hydrogen phosphate and 8.20 g (0.0261 mol) of 2-[2-(2,2,2-trifluoroethoxy)phenoxy]ethyl methane sulfonate followed by addition of 4.0 g (0.0055 mol) of tetra butyl ammonium iodide and stirred the reaction mass at 85-90° C. for 10-12 h. Added a solution of 4.4 g of sodium hydroxide dissolved in 10 ml of water and stirred the reaction at ambient temperature till completion. Added demineralized water and toluene and stirred at room temperature for half an hour. Separated the toluene layer and concentrated under reduced pressure and to the solid mass so obtained were added 110 ml of dimethyl sulfoxide and a solution of 1.95 g (0.0488 mol) of sodium hydroxide dissolved in 7.95 ml of water followed by addition of 7.5 g (0.066 mol) of 30% w/w of hydrogen peroxide. Stirred the reaction mass at room temperature followed by addition of 210 ml of aqueous solution of sodium sulfite and extracted the compound in ethyl acetate. Washed the organic layer with brine and concentrated under reduced pressure to get 10.4 g of crude Silodosin.
N,N-dialkyl impurity is 1.83% as per HPLC Example 2

Purification of Crude Silodosin

To the 10 g (0.0080 mol) of crude mass of Silodosin was added 110 ml of isopropyl alcohol followed by addition of 1.75 g of oxalic acid at ambient temperature. Stirred the solution 6-8 h and filtered the precipitates. Added ethyl acetate and water in the ratio of 1:1 to the above solid followed by addition of 5 ml of liquor ammonia. Stirred the reaction mass at ambient temperature for 15 min and separated the layers. Concentrated the organic layer to ¼ of its volume and left undisturbed overnight. Filtered the precipitates and recrystallized with ethyl acetate followed by drying under reduced pressure to get 5.1 g of pure Silodosin. The amount of impurities and the percent impurity of the Silodosin obtained was as follows:
N,N-dialkyl impurity: undetectable amount
Other impurities: 0.03 to 0.09%
Silodosin purity: 99.65% (HPLC)

Comparative Examples

To analyze proper salt preparation and isolation of solid precipitates after purification of Silodosin, the crude Silodosin obtained in Example 1 was purified using different acids for preparation of the acid salt and different solvents for extracting the pure Silodosin. The methodology employed was the same as described in Example 2 above. The acids used were oxalic acid, tartaric acid, acetic acid, hydrochloric acid, sulfonic acid and the solvents used were ethyl acetate, acetone and isopropyl alcohol. The results obtained are tabulated in Table 1 below:

TABLE 1

Different salts of compound of formula IX to remove N,N-dialkyl impurity:

| Experiment | Acids used for salt formation of compound (IX) | Solvent | Result |
| --- | --- | --- | --- |
| 1 | Oxalic acid | Ethyl acetate | Proper salt preparation with isolation of solid precipitates |
| 2 | Tartaric acid | Isopropyl alcohol | No salt preparation |
| 3 | Tartaric acid | Ethyl acetate | No salt preparation |
| 4 | Oxalic acid | acetone | Sticky mass isolated |
| 5 | Tartaric acid | acetone | No salt preparation |
| 6 | Acetic acid | Acetone or ethyl acetate | No salt preparation |
| 7 | Hydrochloric acid | Isopropyl alcohol or ethyl acetate | No salt preparation |
| 8 | Sulfonic acid | Isopropyl alcohol | Sticky mass isolated |
| 9 | Acetic acid | Isopropyl alcohol and/or ethyl acetate | No salt preparation |

The results indicate that proper salt formation with isolation of solid precipitates of Silodosin occurs only when an oxalic acid salt of Silodosin is prepared and extracted with ethyl acetate as employed in the present invention (Experiment 1). In contrast, in the comparative experiments 2-9, either show no salt preparation or result in a sticky mass.

In accordance with the teachings of the present invention, there is minimal to no loss of solvents is involved in the process, hence making process environment friendly. Also time span for preparation of Silodosin is drastically reduced due to less number of isolations, making process highly economical. It is been observed that use of smaller moles of side chain, 2-[2-(2,2,2-trifluoroethoxy)phenoxy]ethyl methane sulfonate in combination with phase transfer catalyst like tetrabutyl ammonium iodide, 16-crown ether and the like, resulted in the formation of a less amount of N,N- dialkyl impurity which can be effortlessly removed up to 0.01-0.03% at the last stage of production process i.e. at crude Silodosin.

Hence, it can be summarized from the above experiments that multiple and repeated purifications are certainly not required to synthesize DMF (Drug Master File) grade Silodosin.

We claim:
1. A process for the preparation of Silodosin represented by Formula I;

Formula (I)

wherein the process comprises the steps of:
a) condensing chiral compound represented by Formula (III)

Formula (III)

wherein, Bz represents to Benzoyl group with compound represented by Formula (IV)

Formula (IV)

wherein, Ms represents to Methanesulfonyl group in presence of a base and a phase transfer catalyst in an organic solvent to give intermediate represented by Formula (V)

Formula (V)

wherein, n is an integer of 1 and 2;

b) without purification converting compound of Formula (V) to de-protected compound represented by Formula (IX) in an organic solvent;

Formula (IX)

wherein, n is as defined above;
c) without purification converting compound of Formula (IX) to a compound represented by Formula (X)

Formula (X)

wherein n is as defined above;
d) subjecting compound of Formula (X) to purification by converting to an oxalate salt in presence of isopropyl alcohol for removal of N,N-dialkyl impurity represented by Formula (IIc);

Formula (IIc)

e) hydrolysis of the oxalate salt formed in step d) to obtain Silodosin of Formula (I), wherein said Silodosin has N,N-dialkyl impurity in an amount less than 0.03%.

2. The process according to claim 1, wherein in step a) the organic solvent is selected from toluene, acetonitrile, dimethyl sulfoxide and a mixture thereof.

3. The process according to claim 1, wherein the base is selected from sodium hydroxide, dipotassium hydrogen phosphate, and a mixture thereof.

4. The process according to claim 1, wherein the phase transfer catalyst is selected from crown ether, triglyme, tetrabutyl ammonium bromide, tetrabutyl ammonium chloride, tetrabutyl ammonium iodide and potassium fluoride.

5. The process according to claim 1, wherein the condensation step a) is carried at a temperature ranging from 85-90° C.

6. The process as claimed in claim 1, wherein in step a) the compound of Formula (V) having n=2 is formed in an amount of less than 5%.

7. The process according to claim 1, wherein the compound of Formula (I) obtained in step (e) is isolated with purity ≥99.5%.

8. The process according to claim 1, wherein the compound of Formula (I) obtained in step (e) is isolated with other individual impurities below 0.1%.

9. A process for purification of crude Silodosin of Formula (X);

Formula (X)

wherein, n is an integer of 1 and 2; comprising the steps of:

a) converting crude Silodosin of Formula (X) to its oxalate salt in presence of isopropyl alcohol for removal of N,N-dialkyl impurity of Formula (IIc);

Formula (IIc)

b) hydrolysis of the said oxalate salt to get pure Silodosin of Formula (I)

Formula (I)

wherein said Silodosin has N,N-dialkyl impurity in an amount less than 0.03%.

10. The process according to claim 9, wherein the pure Silodosin of Formula (I) has other individual impurities below 0.1%.

11. The process according to claim 9, wherein the compound of Formula (I) obtained in step (b) is isolated with purity ≥99.5%.

* * * * *

UNITED STATES PATENT AND TRADEMARK OFFICE
CERTIFICATE OF CORRECTION

PATENT NO. : 10,377,710 B2
APPLICATION NO. : 15/512044
DATED : August 13, 2019
INVENTOR(S) : Kuldeep Singh Gangwar Page 1 of 1

It is certified that error appears in the above-identified patent and that said Letters Patent is hereby corrected as shown below:

On the Title Page

In Column 1, insert -- (30) Foreign Application Priority Data, Sep. 18, 2014 (IN) 2688/DEL/2014 --, therefor.

Signed and Sealed this
Eighteenth Day of February, 2020

Andrei Iancu
*Director of the United States Patent and Trademark Office*